US008409593B2

(12) United States Patent
Fonolla Moreno et al.

(10) Patent No.: US 8,409,593 B2
(45) Date of Patent: Apr. 2, 2013

(54) METHODS FOR REDUCING TACKINESS ASSOCIATED WITH A XANTHINE COMPOUND

(75) Inventors: Angeles Fonolla Moreno, Paris (FR); Bertrand Piot, Paris (FR)

(73) Assignee: L'Oreal, Paris (FR)

( * ) Notice: Subject to any disclaimer, the term of this patent is extended or adjusted under 35 U.S.C. 154(b) by 689 days.

(21) Appl. No.: 12/135,643

(22) Filed: Jun. 9, 2008

(65) Prior Publication Data

US 2008/0242645 A1  Oct. 2, 2008

Related U.S. Application Data

(62) Division of application No. 11/305,293, filed on Dec. 19, 2005, now abandoned.

(60) Provisional application No. 60/640,239, filed on Jan. 3, 2005.

(30) Foreign Application Priority Data

Dec. 17, 2004  (FR) ..................................... 04 53051

(51) Int. Cl.
*A61K 9/68* (2006.01)
*A61K 9/28* (2006.01)
*A61K 33/00* (2006.01)
*A61K 31/695* (2006.01)
*A61K 31/74* (2006.01)
*C07D 473/00* (2006.01)
*A61Q 5/12* (2006.01)

(52) U.S. Cl. ..... 424/400; 424/401; 424/724; 424/70.12; 424/78.08; 514/63; 544/267; 544/274

(58) Field of Classification Search .................. 424/400, 424/401, 70.12, 724, 78.08; 544/267, 274; 514/63
See application file for complete search history.

(56) References Cited

U.S. PATENT DOCUMENTS

| 5,194,259 | A | | 3/1993 | Soudant et al. |
| 5,523,090 | A | * | 6/1996 | Znaiden et al. ............... 424/401 |
| 5,980,922 | A | * | 11/1999 | Mackey et al. ............... 424/402 |
| 6,290,941 | B1 | * | 9/2001 | Lahanas et al. ................. 424/69 |
| 6,458,372 | B1 | | 10/2002 | Scordamaglia-Crockett et al. |
| 6,503,412 | B1 | * | 1/2003 | Schroeder ..................... 252/8.86 |
| 2002/0022040 | A1 | * | 2/2002 | Robinson et al. ............. 424/401 |
| 2003/0157088 | A1 | * | 8/2003 | Elliott et al. ............... 424/94.64 |
| 2003/0180242 | A1 | | 9/2003 | Eccard et al. |
| 2003/0180395 | A1 | * | 9/2003 | Bueter .......................... 424/725 |
| 2004/0223935 | A1 | | 11/2004 | Meunier |
| 2006/0045890 | A1 | * | 3/2006 | Gonzalez et al. ............. 424/400 |

FOREIGN PATENT DOCUMENTS

FR  2 845 912  4/2004

OTHER PUBLICATIONS

MacPhillamy, H.B., Drugs from Plants: Plant Science Bulletin, Apr. 1963, vol. 9, Issue 2 pp. 1-15 from internet: URL http://www.botnay.org/PlantScienceBulletin/psb-1963-9-2.p p.*
Raskin et al. Can an apple a Day Keep the Doctor Away?: Current Pharmaceutical Design (2004), 10, pp. 3419-3429.*
Revilla et al. Comparison of Several Procedures Used for the Extraction of Anthocynains From Red Grapes; J. Agric. Food Chem. 1998, 46, pp. 4592-4597.*
Phillipson, J. New Drugs From Nature—It Could Be Yew; Phytotherapy Research 13 (1999) pp. 2-8.*

* cited by examiner

*Primary Examiner* — Abigail Fisher
(74) *Attorney, Agent, or Firm* — Oblon, Spivak, McClelland, Maier & Neustadt, L.L.P.

(57) ABSTRACT

The invention relates to a composition containing, preferably in a physiologically acceptable medium, at least one xanthine base or a plant extract containing it, at least one polyurethane powder, and at least one non-ionic dimethicone copolyol. The invention also relates to a cosmetic method for combating cellulite and/or "orange-peel" skin and/or slimming the figure, comprising the application of the composition to the skin. The composition applied to the skin exhibits good cosmetic properties of softness and of non-tackiness.

20 Claims, No Drawings

METHODS FOR REDUCING TACKINESS ASSOCIATED WITH A XANTHINE COMPOUND

REFERENCE TO PRIOR APPLICATIONS

This application claims priority to U.S. Ser. No. 11/305,293 filed Dec. 19, 2005, provisional application 60/640,239 filed Jan. 3, 2005, and to French patent application 04 53051 filed Dec. 17, 2004, the entirety of which is hereby incorporated by reference.

FIELD OF THE INVENTION

The present invention relates to a composition comprising at least one dimethicone copolyol, at least one xanthine base and at least one polyurethane powder. The invention also relates to a method for combating cellulite and/or "orange-peel" skin and/or slimming the figure, comprising the topical application of the composition to the skin.

Additional advantages and other features of the present invention will be set forth in part in the description that follows and in part will become apparent to those having ordinary skill in the art upon examination of the following or may be learned from the practice of the present invention. The advantages of the present invention may be realized and obtained as particularly pointed out in the appended claims. As will be realized, the present invention is capable of other and different embodiments, and its several details are capable of modifications in various obvious respects, all without departing from the present invention. The description is to be regarded as illustrative in nature, and not as restrictive.

BACKGROUND OF THE INVENTION

Adiposity (or excess fat in the subcutaneous cellular tissue) can have many causes that are more or less complex.

Some skin cells, called adipocytes, contain variable amounts of fats in the form of triglycerides, these triglycerides being synthesized in vivo by the adipocytes themselves, according to enzymatic-type reactions (lipogenesis), from the free fatty acids and the glucose (after degradation of the latter to glycerol) contained in the body and introduced therein through certain foods. Now, in parallel, the triglycerides thus formed, and then stored, in the adipocyte cells can also redecompose, still under the action of specific enzymes (lipolysis) contained in these same cells, this time releasing, firstly, fatty acids and, secondly, glycerol and/or monoesters and/or diesters of glycerol. The fatty acids thus released can then either diffuse in the body in order to be consumed therein or converted in different ways, or can be taken up again (immediately or a little later) by the adipocytes in order to again generate triglycerides by lipogenesis.

If, for various reasons (overly rich food, inactivity, ageing and the like), a substantial imbalance becomes established in the body between lipogenesis and lipolysis, i.e., more precisely, if the amounts of fats formed by lipogenesis become appreciably and constantly greater than those which are eliminated by lipolysis, an accumulation of triglycerides then takes place in the adipocytes, which, if it becomes excessive, may be reflected gradually by the appearance of thick skin, the surface of which is often non-uniform ("orange-peel skin") and of more or less flaccid or gelatinous consistency, finally giving the figure a general ungraceful appearance which may evolve from a simple local excess (lipodysmorphia) and the formation of cellulite, passing through a certain level of stoutness and ending at real obesity.

Now, given in particular the deep discomfort, both physical and aesthetic and sometimes psychological, that adiposity and cellulite cause among individuals who are affected by them, in particular among women, they nowadays constitute a condition that is increasingly less well tolerated or accepted.

Solutions have therefore been proposed, in the prior art, for intervening on fatty acid metabolism, which is, as has been seen, one of the favoured targets in the control of this excess of fats in adipocytes.

This can be modulated:

either by blocking glucose transport inside the adipocyte, which results, as has been seen, in a decrease in fatty acids entering the adipocyte, or by inhibition of lipoprotein lipase, or by activation of triglyceride lipase (or hormone-sensitive lipase), generally by stimulating cyclic AMP, for example by activation of adenyl cyclase, or by causing accumulation thereof by inhibition of phosphodiesterase.

Other biological approaches have been explored for acting on the mechanism of lipogenesis and/or of lipolysis. It has thus been proposed to use neuropeptide Y (NPY) receptor antagonists, neuropeptide Y being a neuromediator involved in a certain number of physiological processes and the involvement of which in the regulation of lipolysis it has been possible to demonstrate (P. Valet, *J. Clin. Invest.*, 1990, 85, 291-295). It is also possible to use $\alpha_2$ receptor antagonists or alternatively β3-adrenergic receptor agonists.

The cosmetic compositions proposed to date for the purpose of treating adiposity therefore contain "slimming" compounds which act on one or more of the mechanisms mentioned above. Among these, mention may more particularly be made of xanthine bases (i.e. xanthine derivatives), such as theophylline, caffeine, theobromine.

However, xanthine bases such as caffeine have the drawback of conferring on the slimming compositions poor cosmetic properties that are experienced by the user after application of the composition to the skin. The treated skin exhibits a tacky effect, feels taut and lacks softness: these harmful properties are not satisfactory to the user.

SUMMARY OF THE INVENTION

One object of the present invention is to provide a composition with a slimming action containing a xanthine base and exhibiting good cosmetic properties after application of the composition to the skin, in particular good properties of non-tackiness and of softness.

The inventors have discovered that such a composition can be obtained by using, with a xanthine base, a polyurethane powder and a non-ionic dimethicone copolyol.

The composition applied to the skin does not exhibit any tacky effect and gives the skin a pleasant feeling of softness, without any effect of tautness. In addition, the composition exhibits good slimming effectiveness.

DETAILED DESCRIPTION OF THE PREFERRED EMBODIMENTS

A primary subject of the invention is a composition comprising, preferably in a physiologically acceptable medium, at least one xanthine base and/or at least one plant extract containing a xanthine base, at least one polyurethane powder and at least one non-ionic dimethicone copolyol.

Another subject of the invention is a method for combating cellulite and/or "orange-peel" skin and/or slimming the figure, comprising the application to the skin of a composition as defined above.

The composition according to the invention is most preferably generally suitable for topical application to the skin, and therefore preferably comprises a physiologically acceptable medium, i.e. a medium compatible with the skin. It is preferably a cosmetically acceptable medium, i.e. a medium that has a pleasant colour, smell and feel, and that does not generate any unacceptable discomfort (stinging, tautness, redness) that may put the consumer off using this composition.

The composition according to the invention comprises at least one xanthine base and/or a plant extract containing it.

Among xanthine bases that can be used according to the invention, mention may be made of: caffeine, theophylline, theobromine, acefylline, xanthinol nicotinate, diniprophylline, diprophylline, etamiphylline and its derivatives, etophylline, proxyphylline, pentophylline, propentophylline, pyridophylline and bamiphylline, and their mixtures, without this list being limiting.

Use is in particular preferably made of caffeine, theophylline, theobromine and acefylline, and more particularly caffeine. These xanthine bases are known to be inhibitors of phosphodiesterase, which is the enzyme responsible for the degradation of cAMP. By increasing the intracellular level of cAMP, these xanthine bases promote lipolytic activity and therefore constitute first-rate slimming active agents.

As examples of plant extracts containing xanthine bases, mention may in particular be made of extracts of tea, of coffee, of guarana, of maté and of cola, and their mixtures, without this list being limiting.

The one or more xanthine bases may be present in the composition according to the invention in any amount that is effective for the desired purpose, for example an amount ranging from 0.01% to 10% by weight, relative to the total weight of the composition, preferably ranging from 0.1% to 7% by weight, and preferentially ranging from 0.1% to 3% by weight, in particular ranging from 1% to 3% by weight.

The composition according to the invention also contains at least one polyurethane powder. In particular, the polyurethane powder is preferably not film-forming, i.e. it does not form a continuous film when it is deposited on a support such as the skin.

Advantageously, the polyurethane powder is a powder of a copolymer of hexamethylene diisocyanate and of trimethylol hexyl lactone. Such a polyurethane powder is in particular sold under the names "Plastic Powder D-400" and "Plastic Powder D-800" by the company Toshiki.

Another polyurethane powder that may be used is that sold under the name "Plastic Powder CS-400" by the company Toshiki.

The at least one polyurethane powder may be present in the composition according to the invention in any amount that is effective for the desired purpose, for example an amount ranging from 0.5% to 10% by weight, relative to the total weight of the composition, and preferably ranging from 0.5% to 6% by weight, and preferentially ranging from 0.5% to 3% by weight.

The composition according to the invention also comprises at least one non-ionic dimethicone copolyol.

The non-ionic dimethicone copolyol is an oxypropylenated and/or oxyethylenated polydimethylmethylsiloxane which does not contain any ionic groups (such as anionic, cationic or amphoteric groups).

Non-ionic dimethicone copolyols are in particular described in patent U.S. Pat. No. 4,268,499, the contents of which are incorporated into this application by way of reference.

A particularly preferred form of dimethicone copolyol is that sold under the name Dow Corning 5225C by the company Dow Corning.

The one or more non-ionic dimethicone copolyol may be present in the composition according to the invention in any amount that is effective for the desired purpose, for example in an amount ranging from 0.05% to 5% by weight, relative to the total weight of the composition, preferably ranging from 0.1% to 3% by weight, and preferentially ranging from 0.1% to 2% by weight.

The composition according to the invention may advantageously comprise an aqueous phase.

For example, the composition may comprise water in an amount ranging from 30% to 80% by weight, relative to the total weight of the composition, preferably ranging from 40% to 70% by weight, and preferentially ranging from 45% to 65% by weight.

The water may be normal water, a floral water such as cornflower water and/or a mineral water such as eau de Vittel, eau de Lucas or eau de La Roche Posay and/or a spring water, for example.

The aqueous phase may comprise at least one monoalcohol having from 2 to 6 carbon atoms, such as ethanol or isopropanol, in particular in an amount ranging from 1% to 30% by weight, relative to the total weight of the composition, and preferably ranging from 5% to 20% by weight.

The aqueous phase may also comprise salicylic acid or one of its derivatives such as n-octanoyl acid, in particular present in an amount ranging from 0.1% to 5% by weight, relative to the total weight of the composition, preferably ranging from 0.1% to 3% by weight and preferentially ranging from 0.1% to 2% by weight.

While not bound by any particular theory, it is believed that the preferred presence of at least one monoalcohol and of salicylic acid in the aqueous phase promote good dissolving of the xanthine base in the aqueous phase and therefore improve the slimming effectiveness of the composition.

The composition according to the invention may be in any form, including any of the, e.g., cosmetic, dermatological and/or pharmaceutical forms normally used for topical application to the skin, in particular in the form of an oil-in-water or water-in-oil or multiple emulsion, that is optionally gelled, of a silicone emulsion, of a microemulsion or nanoemulsion, of a liquid, pasty or solid anhydrous product, or of a dispersion of oil in an aqueous phase in the presence of spherules, it being possible for these spherules to be polymeric nanoparticles such as nanospheres and nanocapsules or, better still, lipid vesicles of ionic and/or non-ionic type. Advantageously, the composition is in the form of an oil-in-water emulsion.

The composition of the invention may be more or less fluid and may have the appearance of a white or coloured cream, of an ointment, of a milk, of a lotion, of a serum, of a paste, of a mousse or of a gel. It may optionally be applied to the skin in the form of an aerosol. It may also be in the form of a solid, and for example in the form of a stick.

The composition of the invention may also contain the adjuvants known in the cosmetic and dermatological fields such as hydrophilic or lipophilic gelling agents, hydrophilic or lipophilic active agents, moisturizers (such as glycerol, propylene glycol, butylene glycol, pentylene glycol, hexylene glycol, dipropylene glycol or diethylene glycol), preserving agents, antioxidants, solvents, fragrances, fillers, pigments, hydrophilic screening agents, odour absorbers and dyestuffs. The amounts of these various adjuvants are those conventionally used in the fields under consideration and are, for example, from 0.01 to 20% of the total weight of the composition. Depending on their nature, these adjuvants can be introduced into the fatty phase, into the aqueous phase, or into lipid vesicles and/or into nanoparticles.

When the composition according to the invention is an emulsion, the proportion of the fatty phase can preferably range from 5 to 50% by weight, and preferably from 5 to 30% by weight relative to the total weight of the composition.

As fats that can be used in the invention, use may be made for example of mineral oils, oils of animal origin, synthetic oils, silicone oils and fluoro oils. Fatty acids, waxes and gums, and in particular silicone gums, can also be used as fats.

The emulsifiers and co-emulsifiers optionally used in the composition in the form of an emulsion include those chosen from those known and used in the field under consideration. These emulsifiers and co-emulsifiers are preferably present, in the composition, in a proportion ranging from 0.3 to 20% by weight, and preferably from 0.5 to 5% by weight relative to the total weight of the composition. As emulsifiers and co-emulsifiers that can be used in the invention, it is particularly advantageous to use the fatty acid esters of a polyol such as PEG-100 stearate, PEG-50 stearate and PEG-40 stearate; sorbitan tristearate, the oxyethylenated sorbitan stearates available under the trade names Tween® 20 or Tween® 60, for example; and mixtures thereof.

As hydrophilic gelling agents, mention may in particular be made of carboxyvinyl polymers (carbomer), acrylic copolymers such as acrylate/alkyl acrylate copolymers, polyacrylamides, polysaccharides, natural gums and clays, and as lipophilic gelling agents, mention may be made of modified clays such as bentones, metal salts of fatty acids, and hydrophobic silica.

As active agents which will add to the action of the slimming active agents according to the invention, use may in particular be made of:
active agents that act on the microcirculation (vasoprotectors or vasodilators), such as flavonoids, extracts of *Gingko biloba,* ruscogenins, esculosides, escin extracted from horsechestnut, nicotinates, hesperidin methyl chalcone, butcher's broom, essential oils of lavender or of rosemary;
firming active agents and/or anti-glycant active agents (which prevent the binding of sugar to collagen fibres), such as extracts of *Centella asiatica* and of St. Paul's wort, which stimulate collagen synthesis, silicon, amadorine, vitamin C and its derivatives and retinol and its derivatives;
and mixtures thereof.

Of course, those skilled in the art know to choose the optional compound(s) to be added to the compositions according to the invention, and also the concentration thereof, in such a way that the advantageous properties intrinsically associated with the compositions in accordance with the invention are not, or are not substantially, adversely affected by the addition envisaged.

The composition defined above can be used to prevent or combat cellulite and/or to refine the figure or the contours of the face.

The invention will now be illustrated by means of the following nonlimiting examples.

EXAMPLES 1 TO 4

3 slimming compositions according to the invention (Examples 2 to 4) containing a non-ionic dimethicone copolyol and a polyurethane powder, and a composition that is not part of the invention (Example 1) containing an anionic dimethicone copolyol and a silica powder, were prepared.

The composition was applied to the skin and the cosmetic properties obtained were observed.

The contents are expressed in grams.

| COMPOSITION | Example 1* | Example 2 | Example 3 | Example 4 |
|---|---|---|---|---|
| PHASE I | | | | |
| Water | qs | qs | qs | qs |
| Acrylic gelling agent (1) | 0.5 | 0.5 | | 0.2 |
| Xanthan gum | 0.1 | 0.08 | | |
| AMPS (2) | | 0.1 | 1 | 0.6 |
| Glycerol | 4 | 4 | 5 | 4 |
| Propylene glycol | 3 | 3 | 3 | 3 |
| Caffeine | 2.5 | 2.5 | 3 | 4 |
| Salicylic acid | 0.4 | 0.4 | 0.5 | 0.6 |
| PHASE II | | | | |
| Dimethicone copolyol (3) | 0 | 2 | 3 | 5 |
| Volatile silicone oils | 9 | 9 | 7 | 5 |
| Pecosil PS-100 (4) | 1 | — | — | — |
| Silicone gums | 0.5 | 0.5 | 1 | 2 |
| Fragrance | 0.4 | 0.4 | 0.5 | 0.5 |
| PHASE III | | | | |
| Ethanol | 12 | 12 | 16 | 1 |
| PHASE IV | | | | 18 |
| Polyurethane powder (5) | | 1 | 0.8 | 2 |
| Silica | 1 | | | |
| Cosmetic properties | No soft effect. The skin catches and is taut. Tacky sensation. | Soft and slippery effect, not tacky. | Very soft skin, no tacky effect. | Very soft skin, no tacky effect. |

*example not part of the invention
(1) Carboxyvinyl polymer sold under the name "Carbopol 980" by the company Noveon.
(2) Polyacrylamidopropanesulphonic acid partially neutralized with aqueous ammonia and crosslinked, sold under the name "Hostacerin AMPS" by the company Clariant.
(3) Mixture of dimethicone copolyol/cyclopentadimethylsiloxane/water (10/88/2) sold under the name "Dow Corning 5225C Formulation Aid" by the company "Dow Corning."
(4) Oxyethylenated polydimethylsiloxane comprising a phosphate group, sold under the name "Pecosil PS-100" by the company Phoenix Chemical.
(5) Polyurethane powder sold under the name "Plastic Powder D-400" by the company It was noted that the compositions of Examples 2 to 4 according to the invention, after application to the skin, provide a satisfactory softness and do not feel tacky, whereas the composition of Example 1 that is not part of the invention confers a tautness of the skin (no softness) and exhibits a tacky appearance.

The above written description of the invention provides a manner and process of making and using it such that any person skilled in this art is enabled to make and use the same, this enablement being provided in particular for the subject matter of the appended claims, which make up a part of the original description and including a composition comprising, in a physiologically acceptable medium, at least one xanthine base or a plant extract containing it, at least one polyurethane powder, and at least one non-ionic dimethicone copolyol. Also fully enabled is a cosmetic method for combating cellulite and/or "orange-peel" skin and/or slimming the figure, comprising the topical application to the skin of a composition according to the invention. In a preferred embodiment, the skin to which the composition is applied is skin showing signs of cellulite, or skin areas that commonly show cellulite with the aging process, etc.

As used above, the phrases "selected from the group consisting of," "chosen from," and the like include mixtures of the specified materials.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out. Terms such as "contain(s)" and the like as used herein are open terms meaning 'including at least' unless otherwise specifically noted.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

The invention claimed is:

1. A method for reducing tackiness associated with xanthine compound(s) in a composition containing at least one xanthine base, comprising adding at least one polyurethane powder and at least one non-ionic dimethicone copolyol to the composition in an amount sufficient to reduce tackiness associated with the xanthine compound(s), wherein the xanthine base is present in the composition in an amount ranging from 0.01% to 10% by weight, the polyurethane powder in an amount ranging from 0.5% to 10% by weight, and the non-ionic dimethicone copolyol in an amount ranging from 0.05% to 5% by weight, all weights being relative to the total weight of the composition.

2. The method according to claim 1, wherein the at least one xanthine base is selected from the group consisting of caffeine, theophylline, theobromine, acefylline, xanthinol nicotinate, diniprophylline, diprophylline, etamiphylline, etophylline, proxyphylline, pentophylline, propentophylline, pyridophylline, bamiphylline, and mixtures thereof.

3. The method according to claim 1, wherein the at least one xanthine base is selected from the group consisting of caffeine, theophylline, theobromine, acefylline, and mixtures thereof.

4. The method according to claim 1, wherein the xanthine base is present in the composition in an amount ranging from 1% to 3% by weight, relative to the total weight of the composition.

5. The method according to claim 1, wherein the polyurethane powder is not film-forming.

6. The method according to claim 1, wherein the polyurethane powder is a powder of a copolymer of hexamethylene diisocyanate and of trimethylol hexyl lactone.

7. The method according to claim 1, wherein the composition comprises a polyurethane powder in an amount ranging from 0.5% to 3% by weight relative to the weight of the total composition.

8. The method according to claim 1, wherein the non-ionic dimethicone copolyol is an oxypropylenated and/or oxyethylenated polydimethylmethylsiloxane that does not contain an ionic group.

9. The method according to claim 1, wherein the non-ionic dimethicone copolyol is present in the composition in an amount ranging from 0.1% to 2% by weight relative to the total weight of the composition.

10. The method according to claim 1, wherein the composition further comprises an aqueous phase comprising water.

11. The method according to claim 10, wherein the composition comprises water in an amount ranging from 30% to 80% by weight, relative to the total weight of the composition.

12. The method according to claim 10, wherein the aqueous phase further comprises at least one monoalcohol having from 2 to 6 carbon atoms.

13. The method according to claim 12, wherein the aqueous phase comprises at least one of ethanol and isopropanol.

14. The method according to claim 12, wherein the at least one monoalcohol is present in the composition in an amount ranging from 1 to 30% by weight, relative to the total weight of the composition.

15. The method according to claim 1, wherein the composition comprises at least one salicylic acid compound selected from the group consisting of salicylic acid, n-octanoyl salicylic acid, and mixtures thereof.

16. The method according to claim 15, wherein the salicylic acid compound is present in the composition an amount ranging from 0.1% to 5% by weight, relative to the total weight of the composition.

17. The method according to claim 1, wherein the composition is in the form of an oil-in-water emulsion.

18. The method according to claim 1, wherein the composition further comprises at least one active agent chosen from active agents that act on microcirculation, firming active agents, anti-glycant active agents, and mixtures thereof.

19. The method according to claim 1, wherein the composition comprises, relative to the total weight of the composition: 0.1% to 7% by weight of said at least one xanthine base; 0.5% to 6% by weight of said at least one polyurethane powder; and 0.1% to 3% by weight of said at least one non-ionic dimethicone copolyol.

20. The method according to claim 1, wherein the composition comprises, relative to the total weight of the composition: 1% to 3% by weight of said at least one xanthine base; 0.5% to 3% by weight of said at least one polyurethane powder; and 0.1% to 2% by weight of said at least one non-ionic dimethicone copolyol.

* * * * *